United States Patent [19]

Ranken

[11] Patent Number: 5,084,213

[45] Date of Patent: Jan. 28, 1992

[54] MIXED HALOGENATION OF CYCLODODECATRIENE

[75] Inventor: Paul F. Ranken, Baton Rouge, La.

[73] Assignee: Ethyl Corporation, Richmond, Va.

[21] Appl. No.: 487,841

[22] Filed: Mar. 5, 1990

[51] Int. Cl.$^5$ ............................................. C09K 21/00
[52] U.S. Cl. ..................................... 252/601; 252/604; 524/142
[58] Field of Search .................. 252/601, 604; 524/142

[56] References Cited

U.S. PATENT DOCUMENTS

| 3,558,727 | 1/1971 | Jenkner et al. | 260/648 |
| 3,652,688 | 3/1972 | Olechowski et al. | 260/648 R |
| 3,833,675 | 9/1974 | Newcombe et al. | 260/648 |
| 3,912,792 | 10/1975 | Touval | 260/863 |
| 3,950,456 | 4/1976 | Newcombe | 260/880 R |
| 4,020,250 | 4/1977 | Lal | 526/13 |
| 4,021,406 | 5/1977 | Touval | 260/45.75 B |
| 4,052,468 | 10/1977 | Peterson et al. | 260/648 F |
| 4,067,930 | 1/1978 | Versnel et al. | 260/880 R |
| 4,127,559 | 11/1978 | Newcombe | 260/45.75 B |
| 4,255,323 | 3/1981 | Barkis et al. | 260/45.75 B |
| 4,368,233 | 1/1983 | Barkis et al. | 428/245 |
| 4,980,382 | 12/1990 | Sonnenberg et al. | 521/60 |

Primary Examiner—Robert L. Stoll
Assistant Examiner—N. Bhat
Attorney, Agent, or Firm—Terry B. Morris; David E. LaRose; Richard L. Hansen

[57] ABSTRACT

Composition of heterohalogenated cyclododecatriene (e.g. $C_{12}H_{18}Br_xCl_y$) are disclosed and methods for preparation thereof.

8 Claims, No Drawings

MIXED HALOGENATION OF CYCLODODECATRIENE

The present invention relates to novel methods of halogenating cyclododecatriene and derivatives thereof to produce novel halogenated cyclododecane compositions, such having both bromine and chlorine atoms.

BACKGROUND OF INVENTION

Halogenating cyclododecatriene with one kind of the several halogens (e.g. bromine) used to halogenate multi-unsaturated cycloaliphatic hydrocarbons is known. See U.S. Pat. No. 3,652,688 (Olechowski et al). Halogenating with more than one kind of halogen (i.e. "mixed halogenating" or "heterohalogenating") is known for polycyclic compounds having use as flame retardants. Although some of these polycyclic compounds have a cyclododecyl adduct, only one kind of halogen is added to the cyclododecyl adduct ring. See U.S. Pat. No. 4,067,930 (Versnel et al). There remains a need for novel compositions and methods of making thereof relating to cyclododecatriene to permit greater flexibility in utilizing halogenated cyclododecatriene derivatives, particularly in flame retardancy material.

SUMMARY

The present invention comprises novel methods of halogenating cyclododecatriene to produce novel halogenated cyclododecane compositions. The halogenation results in a cyclododecyl compound having multiple halogen (e.g. bromine and chlorine) additions.

DESCRIPTION OF THE PREFERRED EMBODIMENTS

One embodiment of the present invention is the novel compositions expressed in the empirical formula $C_{12}H_{18}Br_xCl_y$, where x and y are each at least greater than zero. The present invention is generally usable where the singularly halogenated hexabromocyclododecane is used. For example, 1,2,5,6-tetrabromo-9,10-dichlorocyclododecane can be substituted for or used in conjunction with hexabromocyclododecane, such as for use as a fire retardant.

Preferably, the sum of x+y is at least about 2 and at most about 6 and x and y are both independently each at least about 1. More preferably, the sum of x+y is at least about 4 and at most about 6 and x and y are both independently each at least about 2. Preferably, the ratio x/y is from about 1/1 to about 2/1. A preferred precursor in the production of the present invention comprises cyclododecatriene. The preferable halogen value (i.e. x+y) is that value indicative of complete addition at all available double bonds in the precursor reactant mixture, taking into consideration the possible presence of partially saturated or halogenated or otherwise reacted derivatives, e.g. x+y=6 for a pure cyclododecatriene reactant mixture composed of only cyclododecatriene but less than 6 if there is present some amount of 1,5-cyclododecadiene in the reactant mixture. An advantage of the invention is the capability provided wherein the ratio of the differing halogens is adjustable to be tailored to optimize the compound's intended use.

Other embodiments of the present invention are processes for producing the novel compositions. Processes in accordance with the present invention comprise the halogenating of a cyclododecatriene reactant with a halogenating agent.

The halogenating agent is preferably selected from a group consisting of bromine, chlorine, bromine chloride, iodine bromide and iodine chloride. The more preferred agents are bromine, chlorine and bromine chloride. Most preferred is bromine chloride. Halogenation can be performed with the halogenating agent in a neat (i.e. solventless) environment or with a solvent. For example, liquid cis,trans,trans-1,5,9-cyclododecatriene can be halogenated with liquid bromine chloride at ambient temperature and pressure. The reaction mass yields a solid product susceptible to water or solvent washing or slurrying to remove unreacted compounds. The solvent used can be an $C_1$–$C_6$ linear or branched alkyl alcohol (e.g. ethanol, i-butanol or propanol), $C_1$–$C_6$ linear or branched alkyl halide (e.g. ethylene dichloride, carbon tetrachloride, methylene dibromide or bromoform), acetic acid, propionic acid, carbon disulfide, or mixtures thereof.

Halogenating in accordance with the present invention can be performed by adding two or more halogens to cyclododecatriene or by adding one or more halogens to a derivative of cyclododecatriene, e.g. cyclododecadiene or tetrabromocyclododecene. The product of this halogenation is a twelve carbon, single ring compound having two different kinds of halogen atoms attached thereto, preferably bromine and chlorine atoms. When reduction derivatives (e.g. those having hydrogen added) of cyclododecatriene are present, the numerical hydrogen value in the empirical formula (i.e. $C_{12}H_{18}Br_xCl_y$) can vary accordingly, but preferably less than five percent. For example, 1,5-cyclododecadiene can be halogenated with bromine chloride to produce 1,5-dibromo-2,6-dichlorocyclododecane or 1,2-dibromo-5,6-dichlorocyclododecane or mixtures thereof. Only partial halogenation can result in producing 5-bromo-6-chloro-cyclododecene-1. Similarly, 1,5,9-cyclododecatriene can be only partially halogenated to produce, for example, 5,6-dibromo-9,10-dichlorocyclododec-1-ene or 5,9-dibromo-6,10-dichlorocyclododec-1-ene.

The halogenating can be either a one-step or a two-step process. For example, cyclododecatriene can be mixed halogenated by reaction with bromine chloride in a one-step halogenation process, resulting in both bromine and chlorine atoms being added. However, halogenation can proceed by a first step halogenation of cyclododecatriene to a partially halogenated cyclododecatriene compound, e.g. tetrabromocyclododecene. A second step halogenation, such as with chlorine or bromine chloride, can then be carried out to produce a mixed halogenated product, e.g. 1,2,5,6-tetrabromo-9,10-dichlorocyclododecane product.

Halogenation can be performed at stoichmetric quantities. However, it is preferred that an excess of halogen should be present, such as up to 50% excess based on stoichmetric amounts. More preferably, a slight excess can be present (e.g. from about 1% to about 15%); most preferably, from about 2% to about 3%.

Suprisingly, mixed halogenation of cyclododecatriene is particularly advantageous over a halogenation with only one kind of halogen, e.g. hexabromocyclododecane, in that mixed halogenation is faster than halogenation by a single halogen (as much as ten times). Synergism of the fire retardancy function also occurs because of the presence of differing kinds of halogens. Therefore, it is especially preferred that there be at least two different halogens attached to the cyclododecyl olefin reactant used in accordance with this invention.

The exothermic halogenation reaction advantageously are carried out at a temperature of from about 10° C. to about 50° C., preferably at about 20°–45° C., most preferably about 40°–45° C. Reaction temperatures below about 10° C. and above about 50° C. can be used but may not be preferrable due to side reactions or economic considerations. Ambient pressure is preferred but superatmospheric or subatmospheric pressures could also provide mixed halogenated cyclododecanes.

After completion of the reaction, purification is performed, such as by reslurrying or washing with water or solvent to remove unwanted compounds. Further purifying techniques, such as filtration, centrifugation and drying, can be used similar to methods used in the production of hexabromocyclododecane. For example, see U.S. Pat. Nos. 3,558,727 (Jenkner et al) and 3,833,675 et al) incorporated in their entirety herein by reference.

The preferred flame retardant of this invention is mixed halogenated cyclododecatriene-1,5,9. Complete halogenation yields halogenated cyclododecane having no unsaturated bonds. When the mixed halogen used is bromine chloride (BrCl), the preferable product has four bromine atoms and two halogen atoms, being either (1) one bromine and one chlorine or (2) two chlorine atoms. An illustrative product is either 1,2,5,6,9-pentabromo-10-chlorocyclododecane or 1,2,5,6-tetrabromo-9,10-dichlorocyclododecane. It is possible to have competing reactions in these systems where, for example, reaction products composed of not solely either one or the other of the above products, but rather of a mixture of these two, as well as other products are formed. This can include some reaction products which are only partially halogenated. Separation of the reaction products into collections of several different products can be difficult, uneconomical or impossible. However, a reaction product composing a mixture of these separate individual products is still usable as a fire retardant.

The following, non-limiting example illustrates this concept in one embodiment of this invention:

EXPERIMENT

A flask was charged with 37 grams of isobutanol and 49 grams of chloroform. This solvent system was mechanically stirred and had cis, trans, trans-1,5,9-cyclododecatriene (CDT) and bromine chloride [BrCl] added to it at the rate indicated below at spatially different locations. The BrCl was premixed in chloroform before addition to the solvent system. Over a two and one-quarter hour period a first quantity of 38.8 grams of CDT and a second quantity of 85.6 grams of BrCl premixed in 100 grams of chloroform were fed simultaneously into the solvent system, all of which constituted a reaction mass that was maintained at a temperature of 40°–45° C. After completion of the addition of the CDT and BrCl quantities, the reaction mass was stirred for fifteen minutes.

The reaction mass was allowed to stand at room temperature three days, after which it was stirred and neutralized to pH 7 with 45.5 grams of 20 weight percent aqueous sodium carbonate. The solids in the reaction mass were collected by suction filtration. These solids were rinsed with a solution of 24 grams of chloroform and 6 grams of isobutyl alcohol. A second washing of the solids was done with 300 milliliters of water. The solids were then air dried and vacuum dried.

Forty-eight grams of white solids with a melting point range of 183°–191° C. were isolated. Bromine content of 54% by weight and chlorine content of 14% were determined by using a standard wet analytical sodium/biphenyl method of determining halogen content. From this determination a molecular weight of 514 and an empirical formula of $C_{12}H_{18}Br_{3.5}Cl_2$ were calculated for this solid product.

It is obvious that many variations can be made in the products and processes set forth above without departing from the scope and spirit of this invention.

What is claimed is:

1. A flame retardant composition which comprises the reaction product of one or more halogen reactants selected from the group consisting of bromine, bromine chloride, iodine bromide and iodine chloride and cyclododecatriene, said halogen reactant(s) being selected so that there are at least two different halogens attached to said reaction product.

2. The composition of claim 1 wherein said halogen reactant is bromine chloride.

3. The composition of claim 1 wherein said reaction product is at least partially halogenated with bromine and chlorine.

4. The composition of claim 3 wherein said reaction product is completely saturated.

5. The composition of claim 3 wherein said reaction product comprises $C_{12}H_{18}Br_xCl_y$ wherein the sum $x+y$ is at least about 2 and at most about 6 and x and y are both independently each at least about 1.

6. The composition of claim 5 wherein the sum of $x+y$ is at least about 4 and at most about 6 and x and y are both independently each at least about 2.

7. The composition of claim 5 wherein x is about 3.5.

8. The composition of claim 5 wherein said reaction product comprises cyclododecane having four bromine atoms and two halogen atoms selected from the group consisting of bromine and chlorine such that at least one atom is chlorine.

* * * * *